(12) United States Patent  
Garcia Molina et al.

(10) Patent No.: US 10,064,578 B2  
(45) Date of Patent: Sep. 4, 2018

(54) SENSORY STIMULI TO INCREASE ACCURACY OF SLEEP STAGING

(71) Applicants: KONINKLIJKE PHILIPS N.V., Eindhoven (NL); WISCONSIN ALUMNI RESEARCH FOUNDATION, Madison, WI (US)

(72) Inventors: Gary Nelson Garcia Molina, Madison, WI (US); Sander Theodoor Pastoor, Utrecht (NL); Stefan Pfundtner, Eindhoven (NL); Brady Alexander Riedner, Middleton, WI (US); Michele Bellesi, Madison, WI (US); Giulio Tononi, Verona, WI (US)

(73) Assignees: Koninklijke Philips N.V., Eindhoven (NL); Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/764,063

(22) PCT Filed: Jan. 28, 2014

(86) PCT No.: PCT/IB2014/058591  
§ 371 (c)(1),  
(2) Date: Jul. 28, 2015

(87) PCT Pub. No.: WO2014/118693  
PCT Pub. Date: Aug. 7, 2014

(65) Prior Publication Data  
US 2015/0359482 A1    Dec. 17, 2015

Related U.S. Application Data

(60) Provisional application No. 61/757,757, filed on Jan. 29, 2013.

(51) Int. Cl.  
*A61B 5/00* (2006.01)  
*A61B 5/01* (2006.01)  
(Continued)

(52) U.S. Cl.  
CPC ............. *A61B 5/4812* (2013.01); *A61B 5/01* (2013.01); *A61B 5/0484* (2013.01);  
(Continued)

(58) Field of Classification Search  
CPC ... A61B 5/4812; A61B 5/4806; A61B 5/4821; A61B 5/4815; A61B 5/4818; A61B 5/4809; A61M 21/02  
See application file for complete search history.

(56) References Cited

U.S. PATENT DOCUMENTS

| 6,272,378 B1 | 8/2001 | Baumgart-Schmitt |
| 2004/0193068 A1* | 9/2004 | Burton ................ A61B 5/0476 600/544 |

(Continued)

FOREIGN PATENT DOCUMENTS

RU    2144310 C1    1/2000

OTHER PUBLICATIONS

Doroshenkov et al, "Classification of Human Sleep Stages Based on EEG Processing Using Hidden Markov Models", XP019498013, Biomedical Engineering, vol. 41, No. 1, 2007, pp. 25-28.*

(Continued)

*Primary Examiner* — William Thomson  
*Assistant Examiner* — Vynn Huh (57) ABSTRACT

Systems and methods to detect sleep stages of a subject analyze physiological parameters of the subject in combination with a subject's reactions to stimuli of increasing intensity and/or stimuli having different modalities. Stimuli (Continued)

are provided until a predetermined level of probability is reached for the accuracy of an estimation of the sleep stage of the subject.

18 Claims, 3 Drawing Sheets

(51) Int. Cl.
*A61B 5/0484* (2006.01)
*A61B 5/0488* (2006.01)
*A61B 5/0496* (2006.01)
*A61B 5/08* (2006.01)
*A61B 5/11* (2006.01)

(52) U.S. Cl.
CPC ........... *A61B 5/0488* (2013.01); *A61B 5/0496* (2013.01); *A61B 5/0816* (2013.01); *A61B 5/11* (2013.01)

(56) References Cited

U.S. PATENT DOCUMENTS

| | | | |
|---|---|---|---|
| 2005/0043652 | A1 | 2/2005 | Lovett et al. |
| 2006/0235315 | A1 | 10/2006 | Akselrod et al. |
| 2008/0275314 | A1 | 11/2008 | Mack et al. |
| 2009/0082639 | A1* | 3/2009 | Pittman .............. A61B 5/0205 600/300 |
| 2010/0087701 | A1 | 4/2010 | Berka et al. |
| 2011/0087113 | A1 | 4/2011 | Mack et al. |
| 2011/0319721 | A1* | 12/2011 | Hamaguchi .......... A61B 5/0484 600/300 |

OTHER PUBLICATIONS

Bogen Communications, Inc. "Ambient Noise Sensor Model ANS501 Installation and Use Manual", 2003.*
Mendez et al, "Sleep Staging Classification Based on HRV: Time-Variant Analysis", XP031881177, Proceedings of the 31st Annual International Conference of the IEEE Engineering in Medicine and Biology Society: Engineering the Future of Biomedicine, 2009, pp. 9-12.
Gevins et al, "Classifier-Directed Signal Processing in Brain Research", XP011173869, IEEE Transactions on Biomedical Engineering, vol. BME-19,L No. 12, 1986, pp. 1054-1068.
Pace-Schott et al, "The Neurobiology of Sleep: Genetics, Cellular Physiology and Subcortical Networks", Nature Reviews, Neuroscience, vol. 3, 2002, pp. 591-605.
Massimini et al, "Triggering Sleep Slow Waves by Transcranial Magnetic Stimulation", PNAS, vol. 104, No. 20, 2007, pp. 8496-8501.
Maquet, "The Role of Sleep in Learning and Memory", Science, vol. 294, 2001, pp. 1048-1051.
Velluti, "Interactions Between Sleep and Sensory Physiology", J. Sleep Res., vol. 6, 1997, pp. 61-77.
Sadeh et al, "The Role of Actigraphy in Sleep Medicine", Sleep Medicine Reviews, vol. 6, No. 2, 2002, pp. 113-124.
"Sleep in America" Poll, National Sleep Foundation, 2002, pp. 1-43.
Kim et al, "Markov Analysis of Sleep Dynamics", Physical Review Letters, vol. 102, No. 17, 2009, pp. 1-4.
Reynolds, Stacey, et al., "Sensory Processing, Physiological Stress, and Sleep Behaviors in Children with and without Autism Spectrum Disorders", Occupation, Participation and Health, vol. 32, No. 1, 2012.

* cited by examiner

SENSORY STIMULI TO INCREASE ACCURACY OF SLEEP STAGING

CROSS-REFERENCE TO PRIOR APPLICATIONS

This application is the U.S. National Phase application under 35 U.S.C. § 371 of International Application Serial No. PCT/IB2014/058591, filed on Jan. 28, 2014, which claims the benefit of U.S. Application Ser. No. 61/757,757, filed on Jan. 29, 2013. These applications are hereby incorporated by reference herein.

The present disclosure pertains to systems and methods to detect sleep stages of a subject, and, in particular, increasing the probability of an accurate estimation by analyzing the physiological response of a subject to sensory stimuli.

It is well known that poor or inadequate sleep is both prevalent and medically undesirable. It is known that sleep habits can be improved, assuming the patient is aware of the current quality of his or her sleep. By providing feedback regarding the sleep quality, patients may enact behavioral changes and/or adjust sleep habits in a way that promotes improved sleep quality. It is known that an indication of sleep quality may require identification of different sleep stages during sleep, as well as transitions therebetween. It is known that the sleep stages commonly include a rapid-eye-movement (REM) stage and one or more non-rapid-eye-movement stages (NREMs). It is known that for example polysomnography (PSG) may be used to analyze, detect, and/or determine the current sleep stage of a subject, though there are various problems implementing PSG in a manner that consumers may easily deploy at home without requiring assistance of specialized (medical) personnel.

Accordingly, it is an object of one or more embodiments of the present invention to provide a system to detect sleep stages of a subject. The system comprises a stimulus source configured to provide stimuli to the subject, one or more sensors that generate output signals conveying information related to one or more physiological parameters of the subject, and one or more processors configured to execute computer program modules. The computer program modules comprises a reaction module configured to analyze reactions to stimuli provided by the stimulus source, a sleep stage module, a comparison module, and a stimulus control module. The a sleep stage module is configured to i) generate a sleep stage estimation of the subject based on one or both of the analyzed reactions and/or the one or more physiological parameters, and ii) determine a probability of accuracy of the sleep stage estimation. The comparison module is configured to determine whether the probability of accuracy breaches a predetermined threshold. The stimulus control module is configured to, responsive to the probability of accuracy failing to breach the predetermined threshold, control the stimulus source to provide a reassessment stimulus. The sleep stage module is further configured to reassess one or both of the sleep stage estimation of the subject and/or the probability of accuracy based on an analyzed reaction to the reassessment stimulus provided by the stimulus source.

It is yet another aspect of one or more embodiments of the present invention to provide a method to detect sleep stages of a subject. The method comprises generating output signals conveying information related to one or more physiological parameters of the subject; generating a sleep stage estimation of the subject based on the one or more physiological parameters; determining a probability of accuracy of the sleep stage estimation; determining whether the probability of accuracy breaches a predetermined threshold; providing, responsive to the probability of accuracy failing to breach the predetermined threshold, a reassessment stimulus to the subject; analyzing a reaction to the reassessment stimulus based on one or more physiological parameters; and reassessing one or both of the sleep stage estimation and/or the probability of accuracy based on the analyzed reaction.

It is yet another aspect of one or more embodiments to provide a system configured to detect sleep stages of a subject. The system comprises means for generating output signals conveying information related to one or more physiological parameters of the subject; first means for generating a sleep stage estimation of the subject based on the one or more physiological parameters, wherein the first means is further configured for determining a probability of accuracy of the sleep stage estimation; means for determining whether the probability of accuracy breaches a predetermined threshold; means for providing, responsive to the probability of accuracy failing to breach the predetermined threshold, a reassessment stimulus to the subject; and means for analyzing a reaction to the reassessment stimulus based on one or more physiological parameters. The first means is further configured for reassessing one or both of the sleep stage estimation and/or the probability of accuracy based on the analyzed reaction.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
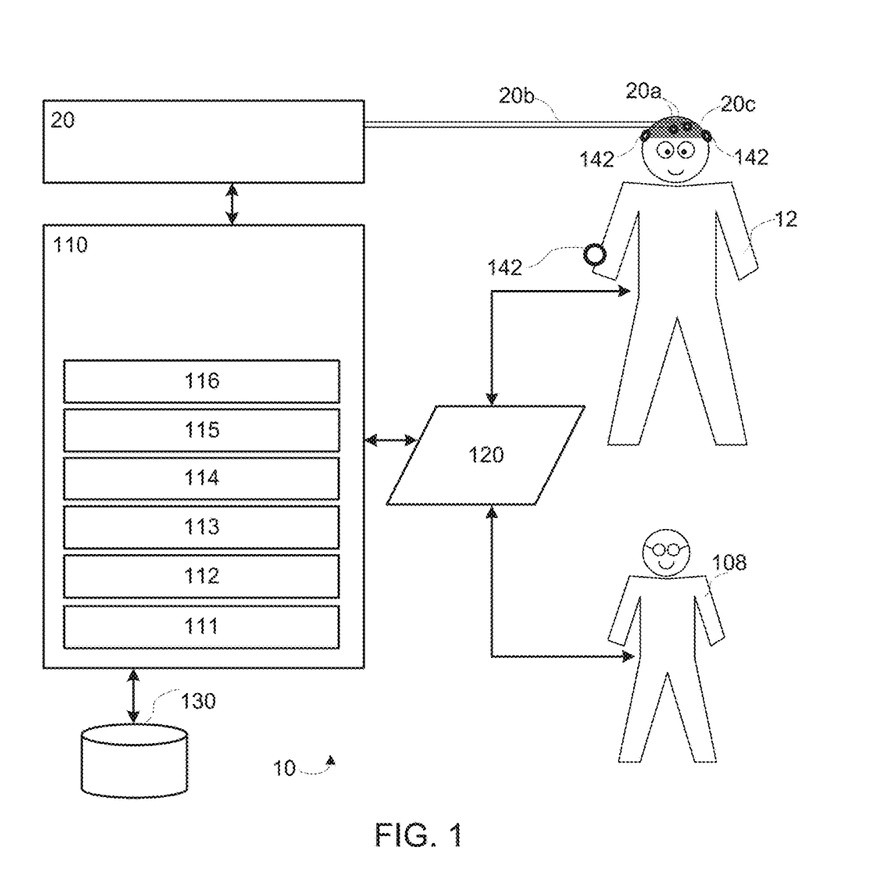
FIG. 1 schematically illustrates a system to detect sleep stages of a subject according to one or more embodiments.

FIG. 1 schematically illustrates a system 10 to detect sleep stages of a subject 12. As used herein, the detection, determination, and/or estimation of a particular sleep stage may interchangeably be referred to as "sleep staging." During sleep, subjects commonly alternate between a REM stage and three or four different NREM stages, depending on the models and/or definitions used. NREM stages as usually referred to as stage 1 through stage 3 or stage 4, as appropriate. Through sleep staging a pattern of stages may be obtained for subject 12. System 10 includes one or more of a stimulus source 20, one or more sensors 142, one or more processors 110, a parameter determination module 111, an electronic storage 1230, a user interface 120, a reaction module 112, a sleep stage module 113, a comparison module 114, a stimulus control module 115, a learning module 116, and/or other components and/or computer program modules.

System 10 may be configured to provide functionality and/or information similar to a PSG study/measurement, but without various complications and downsides typically associated with a PSG study/measurement. System 10 may be configured for (easy-to-use) consumer usage that does not require specialized medical personnel or a (sleep) lab environment. The level of comfort for using system 10 may be improved in comparison to a PSG study/measurement. The number and type of sensors, electrodes, and/or other equipment coupled, connected, and/or attached to the subject for system 10 may be improved in comparison to a PSG study/measurement.

Stimulus source 20 is configured to provide sensory stimuli to subject 12. Sensory stimuli may include visual stimuli, auditory stimuli, tactile stimuli, olfactory stimuli, electromagnetic stimuli, somatosensory stimuli, other sensory stimuli and/or any combination and/or sequence thereof. As used herein, stimuli that are primarily intended for different senses may be referred to as having different modalities. For example, a visual stimulus has a different modality from an auditory stimulus. To some extent, the perception threshold for a particular modality of stimuli may be patient-specific. For example, a particular patient, having exceptional hearing, may have a lower-than-average perception threshold for auditory stimuli. As used herein, the term "perception threshold" refers to a threshold for a measurable reaction or response to a stimulus. The perception threshold may be determined independent of the state of wakefulness and/or sleep stage of a subject. As such, a subject's perception threshold may be different in different sleep stages. For example, a subject may have different perception thresholds for auditory stimuli depending on the current sleep stage. In some embodiments, the different perception thresholds may be used to distinguish between different sleep stages for a particular patient.

Stimulus source 20 may include one or more of a light source, a loudspeaker, an electroacoustic transducer, a vibrating component or device, a device or system configured to produce scents, electrodes 20a, and/or other sources of sensory stimuli or transmitters 20b of sensory stimuli. Stimulus source 20 and/or components included or integrated with stimulus source 20, such as, by way of non-limiting example, electrodes 20a, may be embedded and/or combined with a headband 20c, a hat, a helmet, a wristband, and armband, and/or other objects or combinations of objects that can be worn, used, and/or carried in proximity of subject 12. For example, a light source may need to be positioned in sufficient proximity such that electromagnetic radiation from the light source can impinge on the eyes, eyelids, and/or face of subject 12 to provide a sensory stimulus to subject 12. In some embodiments, operation of, e.g., a loudspeaker included in stimulus source 20 may be adjusted based on the distance between the loudspeaker and subject 12, the level of ambient noise, and/or other environmental considerations, in addition to other considerations described elsewhere herein.

One or more sensors 142 of system 10 in FIG. 1 are configured to generate output signals conveying measurements related to physiological parameters of subject 12. Physiological parameters may include parameters related to brain function/activity, such as electroencephalography (EEG), electromyography (EMG), electrooculography (EOG), parameters related to movement, location, position, tilt, and/or angle of subject 12 and/or a body part of subject 12, respiratory parameters, and/or other parameters.

Figure 2A:
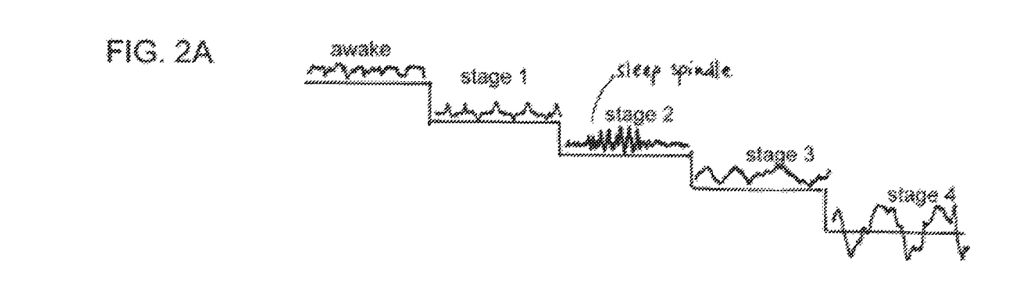
FIGS. 2A-2B-2C illustrate characteristic features of brain activity in various sleep stages.
Figure 2B:
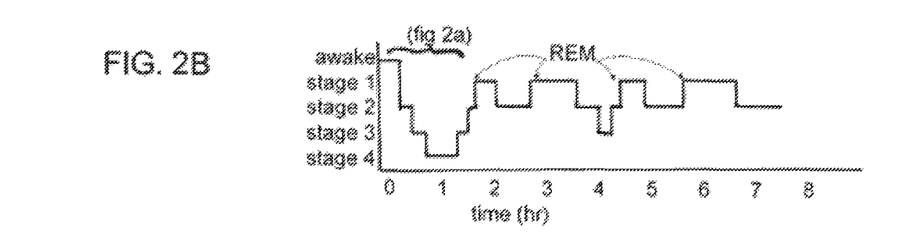
Figure 2C:
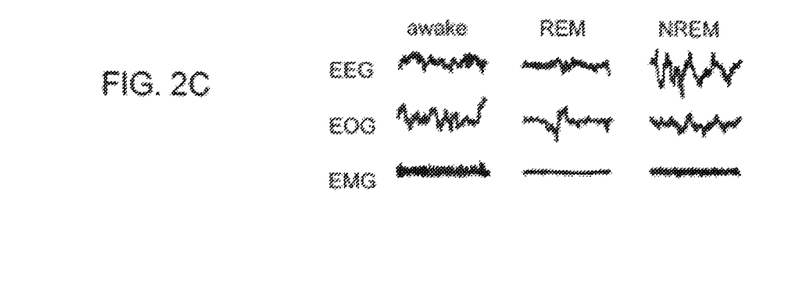

By way of illustration, FIG. 2C illustrates characteristic features of brain activity in various sleep stages. In particular, FIG. 2C illustrates common exemplary graphs for an EEG, an EOG, and an EMG during wakefulness, REM stage and NREM stage. Commonly, such signals may be measured and/or received using one or more electrodes positioned on the head of a subject, for example during a PSG study/measurement. The (average) amplitude of these signals, as well as the specifics of the peaks, troughs, sleep spindles, k-complexes, slow waves, and/or frequency-based characteristics within these signals may be analyzed to distinguish the current sleep stage of a subject. For example, slow waves are known to be more abundant in sleep stage 3 and sleep stage 4, whereas sleep spindles may be more abundant in sleep stage 2.

By way of illustration, FIG. 2B illustrates the progress of a subject through five sleep stages through a period of approximately 8 hours of sleep, as recorded through an EEG. FIG. 2A illustrates approximately the first two hours depicted in FIG. 2B in more detail. For example, FIG. 2A depicts a sleep spindle during stage 2, in which the amplitude increases in the center of the sleep spindle. Analysis of the signals in FIGS. 2B and 2C, for example frequency-based analysis, may be used to distinguish between different sleep stages, e.g. based on different characteristics per sleep stage.

Referring to FIG. 1, the one or more sensors 142 may include an accelerometer, positional sensor, movement sensor, light sensor, infra-red (IR) sensor, electromagnetic sensor, electrode, tilt meter, (video) camera, and/or other sensors. For example, one or more sensors 142 may be configured to generate output signals conveying information pertaining to eye movement of subject 12 (regardless of whether the eyelids of subject 12 are open or closed). Such information which may be used, by way of non-limiting example, to determine whether subject 12 is current in a REM stage or NREM stage.

The illustration of sensor 142 including three members in FIG. 1 is not intended to be limiting. In some embodiments, system 10 may use one or more sensors 142. The illustration of the locations of sensors 142 as depicted in FIG. 1 is not intended to be limiting. An individual sensor 142 may be located at or near (a body part of) subject 12, embedded and/or integrated in a pillow, bed, and/or blanket, and/or at other locations. For example, an individual sensor 142 may include an accelerometer positioned on or near the wrist of subject 12 and used for actigraphy. Resulting signals or information from one or more sensors 142 may be transmitted to processor 110, user interface 120, electronic storage 130, and/or other components of system 10. This transmission may be wired and/or wireless.

The illustration of sensor 142 as being separate and distinct from electrodes 20a is not intended to be limiting. In some embodiments, the same one or more electrodes 20a may be used to provide a stimulus (e.g. in the form of an electrical pulse) and (subsequently) to sense/measure the reaction and/or response of subject 12 to that stimulus.

The one or more sensors 142 may be configured to generate output signals in an ongoing manner during sleep, as well as before or after a period of sleep. This may include generating signals intermittently, periodically (e.g. at a sampling rate), continuously, continually, at varying intervals, and/or in other ways that are ongoing during at least a portion of period of sleep. The sampling rate may be about 1 second, about 10 seconds, about 20 seconds, about 30 seconds, about 40 seconds, about 50 seconds, about 1 minute, about 2 minutes, and/or other sampling rates. It is noted that multiple individual sensors 142 may operate using different sampling rates, as appropriate for the particular output signals and/or parameters derived therefrom. For example, in some embodiments, the generated output signals may be considered as a vector of output signals, such that a vector includes multiple samples of information conveyed related to one or more physiological parameters and/or other parameters. Different parameters may be related to different vectors. A particular parameter determined in an ongoing manner from a vector of output signals may be considered as a vector of that particular parameter.

Electronic storage 130 of system 10 in FIG. 1 comprises electronic storage media that electronically stores information. The electronic storage media of electronic storage 130 may include one or both of system storage that is provided integrally (i.e., substantially non-removable) with system 10 and/or removable storage that is removably connectable to system 10 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 10 to function properly. For example, electronic storage 130 may record or store timing information (including duration of sleep stages and transitions between sleep stages), and/or other parameters (as discussed elsewhere herein), and/or other information. Electronic storage 130 may be a separate component within system 10, or electronic storage 130 may be provided integrally with one or more other components of system 10 (e.g., processor 110).

User interface 120 of system 10 in FIG. 1 is configured to provide an interface between system 10 and a user (e.g., a user 108, subject 12, a caregiver, a therapy decision-maker, etc.) through which the user can provide information to and receive information from system 10. This enables data, results, and/or instructions and any other communicable items, collectively referred to as "information," to be communicated between the user and system 10. An example of information that may be conveyed to user 108 is a report detailing durations of and/or transitions between different sleep stages during a period of sleep or a period of monitoring subject 12. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 12 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 10 from removable storage (e.g., a smart card, a flash drive, a removable disk, etc.) that enables the user(s) to customize system 10. Other exemplary input devices and techniques adapted for use with system 10 as user interface 120 include, but are not limited to, an RS-232 port, RF link, an IR link, modem (telephone, cable, Ethernet, internet or other). In short, any technique for communicating information with system 10 is contemplated as user interface 120.

Processor 110 of system 10 in FIG. 1 is configured to provide information processing capabilities in system 10. As such, processor 110 includes one or more of a digital processor, an analog processor, a digital circuit designed to process information, an analog circuit designed to process information, and/or other mechanisms for electronically processing information. Although processor 110 is shown in FIG. 1 as a single entity, this is for illustrative purposes only. In some embodiments, processor 110 includes a plurality of processing units.

As is shown in FIG. 1, processor 110 is configured to execute one or more computer program modules. The one or more computer program modules include one or more of parameter determination module 111, reaction module 112, sleep stage module 113, comparison module 114, stimulus control module 115, learning module 116, and/or other modules. Processor 110 may be configured to execute modules 111-116 by software; hardware; firmware; some combination of software, hardware, and/or firmware; and/or other mechanisms for configuring processing capabilities on processor 110.

It should be appreciated that although modules 111-116 are illustrated in FIG. 1 as being co-located within a single processing unit, in embodiments in which processor 110 includes multiple processing units, one or more of modules 111-116 may be located remotely from the other modules. The description of the functionality provided by the different modules 111-116 described herein is for illustrative purposes, and is not intended to be limiting, as any of modules 111-116 may provide more or less functionality than is described. For example, one or more of modules 111-116 may be eliminated, and some or all of its functionality may be incorporated, shared, integrated into, and/or otherwise provided by other ones of modules 111-116. Note that processor 110 may be configured to execute one or more additional modules that may perform some or all of the functionality attributed below to one of modules 111-116.

Parameter determination module 111 of system 10 in FIG. 1 is configured to determine one or more physiological parameters and/or other parameters from output signals generated by sensor(s) 142. Operation of parameter determination module 111 may be performed in an ongoing manner. One or more physiological parameters may be determined at different locations and/or positions within system 10 or near subject 12.

Parameter determination module 111 may derive vectors of parameters in an ongoing manner during a period of sleep or a period of monitoring subject 12 from vectors of generated output signals and/or other (vectors of) determined parameters.

Sleep stage module 113 is configured to generate estimations of sleep stages and determine probabilities of accuracy of the generated estimations, for example through a sleep staging algorithm. A sleep staging algorithm may produce a particular estimation and a probability of accuracy that is associated with that particular estimation in conjunction, e.g. simultaneously. Operation of sleep stage module 113 may be based on one or both of analyzed reactions (by reaction module 112) and/or the one or more physiological parameters (as determined by parameter determination module 111).

In some embodiments, sleep stage module 113 may use a model of sleep stage transitions that is based on a Markov-chain. A Markov-chain may use a matrix including elements $p_{ij}$ where i and j are indexes that refer to sleep stages such that $p_{ij}$ indicates the probability of a transition from sleep stage i to sleep stage j. In some embodiments, sleep stage module 113 may use a neural network to determine the probability of accuracy of a sleep stage estimation. The neural network may include a neuron (having a "softmax" activation function) per sleep stage (that the model aims to detect and/or identify) such that the sum of the output values from all neurons is equal to 1. By way of non-limiting example, a model that includes three NREM stages, a REM stage and a wakefulness stage would use five neurons. The output values of each neuron may be interpreted as probabilities. The ideal output of the neural network (in response to input signals that are generated by one or more sensors) would have a 100% probability, i.e. one neuron has an output value of 1 while all other neurons have an output value of zero. More realistic (i.e. non-ideal) outputs of the neural network may be less than 100%. In some embodiments, the accuracy of the neural network may be defined as the difference between the highest two output values among the neurons, thus a values ranging from 0 to 1. Other ways to determine accuracy are contemplated within the scope of this disclosure. It is noted that Markov analysis of sleep dynamics may be implemented in one or more computer program modules of system 10. In some embodiments, the sleep staging algorithm may operate on vectors of physiological parameters, thus taking prior measurements into account.

For consumer-grade implementations, a trade-off between ease of use (including for example comfort) and accuracy/quality of sensor readings may need to be addressed. For example, patients who wish to monitor their sleep habits at home for, by way of non-limiting example, a week, month, or year, may require a higher level of comfort than possible or feasible during a lab-based sleep study of one night.

Comparison module 114 is configured to determine whether the probability of accuracy of a sleep stage estimation (as generated by sleep stage module 113) breaches or exceeds a predetermined threshold of probability. The predetermined threshold of probability may be 60%, 65%, 70%, 75%, 80%, 85%, 90%, 95%, and/or another threshold of probability. Comparison module 114 may be configured to compare the probability of accuracy (as determined by sleep stage module 113) to the predetermined threshold of probability.

In some embodiments, one or more particular sleep stage estimations and the probabilities of accuracy associated with the particular one or more sleep stage estimations may be based on output signals and the parameters derived therefrom, in absence of stimuli being provided to subject 12. In other words, system 10 may be able to detect the current sleep stage with a sufficiently high level of accuracy without providing stimuli to subject 12. As long the predetermined threshold is met or breached for newly generated output signals and physiological parameters, there may be no need to provide stimuli to subject 12. However, if and when the determined probability of accuracy fails to breach the predetermined threshold of probability, the provision of stimuli in conjunction with an analysis of the reactions to such stimuli (through reaction module 112) may produce additional information to reassess and/or refine one or both of the generated sleep stage estimation and/or reassess and/or refine (upwardly) the associated probability of accuracy. In other words, an insufficient level of accuracy for a particular estimation of the current sleep stage may be reassessed and/or refined through the use of a stimulus. Such a stimulus may interchangeably be referred to as a reassessment stimulus. In some embodiments, reassessment stimuli may be provided repeatedly in order to (attempt to) increase the probability of accuracy of the estimation of the current sleep stage. Such a sequence of stimuli may include similar stimuli, stimuli of increasing intensity, stimuli of varying modality, and/or other stimuli and/or combinations thereof.

Responsive to the provision of one or more reassessment stimuli, sleep stage module 113 may be configured to reassess and/or refine one or both of the sleep stage estimation and/or the probability of accuracy. Reassessment may be based on analysis of the reaction of subject 12 to a particular stimulus, such as the analysis performed by reaction module 112.

Stimulus control module 115 is configured to stimulus source 20 to provide stimuli to subject 12. Stimulus control module 115 may be configured to adjust and/or vary the intensity and/or modality of the stimulus that is to be provided to subject 12. For example, the intensity of an auditory stimulus may be adjusted upwardly (i.e. becoming louder) in order to breach the predetermined threshold of probability. Alternatively, and/or simultaneously, stimulus control module 115 may be configured to provide multiple stimuli in conjunction (e.g. simultaneously), in sequence, and/or both. Operation of stimulus control module 115 may be responsive to the probability of accuracy of a sleep stage estimation, as determined by sleep stage module 113, failing to breach a predetermined threshold (of probability). In other words, if the probability of accuracy is sufficiently high in comparison to a predetermined threshold of probability, there may be no need to provide stimuli to subject 12. If the probability of accuracy is not sufficiently high, the provision of stimuli may be used to increase the probability. In some embodiments, control of stimulus source 20 may be based on the sleep stage estimation, and/or other (optionally patient-specific) considerations. For example, the intensity of a particular modality of stimuli may be limited at a predetermined maximum intensity level such that the chance of waking up subject 12 is at an acceptably low level. Such maximum intensity levels may be patient-specific. Alternatively, and/or simultaneously, such maximum intensity levels may be determined and/or estimated through sensory testing while subject 12 is awake.

In some embodiments, stimulus control module 115 may be configured to repeatedly provide stimuli, for example of increasing intensity, until the determined probability of accuracy breaches the predetermined threshold. Stimulus control module 115 may be configured to provide a sequence of stimuli, a combination of stimuli, a sequence of combined stimuli, and/or any permutation of stimuli, sequences, and combinations in an attempt to increase the probability of a sufficiently accurate sleep stage estimation, e.g. up to or above the predetermined threshold of probability.

Operations of stimulus control module 115 may be adjusted based on environmental conditions, such as, by way of non-limiting example, ambient noise. For example, auditory stimuli may need to be intensified in the presence of higher levels of ambient noise.

Reaction module 112 is configured to analyze reactions of subjects to stimuli provided by stimulus source 20. Reaction module 112 may be configured to sample and/or measure one or more particular output signals and/or physiological parameters within a specific period of time. For example, the specific period of time may be selected to fall within a period that is appropriate for a reaction by subject 12 in light of the particular measurements being taken. For example, a reaction by subject 12 as measured through an accelerometer may typically occur 0.5 seconds after a stimulus of a first modality, and typically 0.25 seconds after a stimulus of a second modality. A reaction by subject 12 as measured through electrodes (e.g. an EEG) may typically occur 0.1 seconds after a stimulus of a first modality (e.g. a visual stimulus), and typically 0.2 seconds after a stimulus of a second modality (e.g. an auditory stimulus). As such, the timing of the operations of reaction module 112 may depend with considerable precision of the timing of stimulus control module 115 and/or stimulus source 20. It is noted that these specific periods of time may be patient-specific. It is further noted that for a particular patient, these specific periods of time may gradually change over the course of weeks, moths, and/or other periods of time. By way of non-limiting example, such a gradual change may occur by virtue of a patient becoming accustomed and/or habituated to one or more types of stimuli. For example, the first time the stimuli include the sound of a fire engine in conjunction with the smell of smoke, a particular patient may react rapidly and the stimuli may be very effective. However, by the 100$^{th}$ time these same stimuli are provided, the particular patient may become accustomed to some degree, such that the reaction may be less intense, slower, and/or both.

Learning module 116 is configured to determine the effectiveness of different stimuli. Operation of learning module 116 may be patient-specific. Effectiveness may be quantified by the ability or probability of evoking a reaction in response to a stimulus. Alternatively, and/or simultaneously, such effectiveness may be quantified by the ability or likelihood of increasing the probability of accuracy of the sleep stage estimation by sleep stage module 113. As such, a higher probability of either a reaction or the accuracy of the sleep stage estimation may be commensurate with a higher level of effectiveness. In some embodiments, effectiveness may be quantified by the difference between the level of intensity for a stimulus of a particular modality that evokes at least some predetermined level of response (or increase inaccuracy) and the maximum intensity level for stimuli of that particular modality. Such a level of intensity may be referred to as a responsiveness level of intensity. In other words, if the responsiveness level of intensity in a first modality is close to the maximum intensity level, whereas the responsiveness level of intensity in a second modality is not close to the maximum intensity level, the second modality may be considered more effective than the first modality. Note that the responsiveness level of intensity may vary across different sleep stages. Learning module 116 may be configured to determine which stimulus or set of stimuli is most likely to confirm an estimation of the current sleep stage, optionally on a per-patient basis.

For example, if preliminary measurements of physiological parameters for a particular subject indicate that the current sleep stage is probably stage 2, but the probability of accuracy is insufficient, stimulus control module 115 may be guided, through information from learning module 116, to use visual stimuli in an attempt to increase the probability of accuracy. Assume in this example that learning module 116 has established visual stimuli as an effective way to confirm an estimation of sleep stage 2, at least for this particular subject. For the same subject, at a different moment during the period of monitoring, measurements of physiological parameters may indicate that the current sleep stage is probably stage 4. However, assume that the probability of accuracy of this estimation is insufficient. Responsive to learning module 116 having established that auditory stimuli are an effective way to confirm an estimation of sleep stage 4, at least for this particular subject, stimulus control module 115 may be guided, through information from learning module 116, to use auditory stimuli in an attempt to increase the probability of accuracy. In some embodiments, learning module 116 may be configured to determine different levels of effective intensity for different sleep stages.

Figure 3:
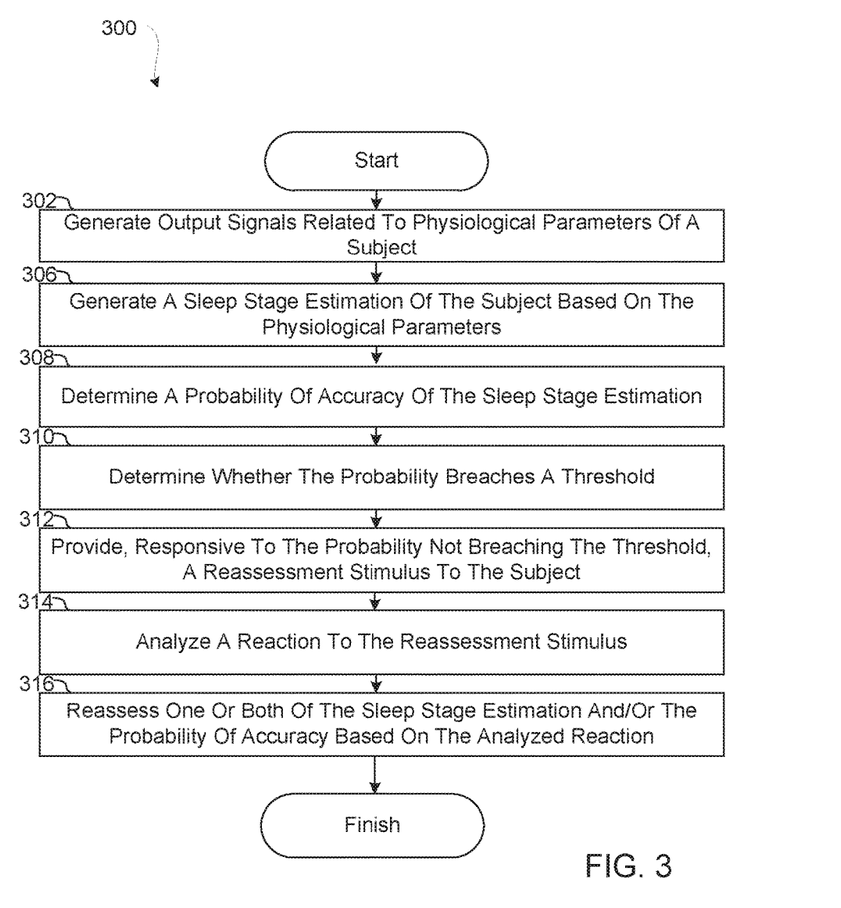
FIG. 3 illustrates a method to detect sleep stages in accordance with one or more embodiments.

FIG. 3 illustrates a method 300 to detect sleep stage of a subject. The operations of method 300 presented below are intended to be illustrative. In certain embodiments, method 300 may be accomplished with one or more additional operations not described, and/or without one or more of the operations discussed. Additionally, the order in which the operations of method 300 are illustrated in FIG. 3 and described below is not intended to be limiting.

In certain embodiments, method 300 may be implemented in one or more processing devices (e.g., a digital processor, an analog processor, a digital circuit designed to process information, an analog circuit designed to process information, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, output signals are generated that convey information related to one or more physiological parameters of the subject. In some embodiments, operation 302 is performed by one or more sensors the same as or similar to sensors 142 (shown in FIG. 1 and described herein).

At an operation 306, a sleep stage estimation of the subject is generated based on the one or more physiological parameters. In some embodiments, operation 306 is performed by a sleep stage module the same as or similar to sleep stage module 113 (shown in FIG. 1 and described herein).

At an operation 308, a probability of accuracy of the sleep stage estimation is determined. In some embodiments, operation 308 is performed by a sleep stage module the same as or similar to sleep stage module 113 (shown in FIG. 1 and described herein).

At an operation 310, it is determined whether the probability of accuracy breaches a predetermined threshold. In some embodiments, operation 310 is performed by a comparison module the same as or similar to comparison module 114 (shown in FIG. 1 and described herein).

At an operation 312, responsive to the probability of accuracy failing to breach the predetermined threshold, a reassessment stimulus is provided to the subject. In some embodiments, operation 312 is performed by a stimulus control module the same as or similar to stimulus control module 115 (shown in FIG. 1 and described herein).

At an operation 314, a reaction to the reassessment stimulus is analyzed based on one or more physiological parameters. In some embodiments, operation 314 is performed by a reaction module the same as or similar to reaction module 112 (shown in FIG. 1 and described herein).

At an operation 316, one or both of the sleep stage estimation and/or the probability of accuracy is reassessed based on the analyzed reaction. In some embodiments, operation 316 is performed by a sleep stage module the same as or similar to sleep stage module 113 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system configured to facilitate sleep stage detection, the system comprising:
a stimulus source configured to provide stimuli to a subject;
one or more sensors that generate output signals conveying information related to one or more physiological parameters of the subject;
an electronic storage configured to store machine readable instructions; and
one or more hardware processors configured by the machine readable instructions to:
analyze, based on the one or more physiological parameters, reactions to the stimuli provided by the stimulus source;
estimate a sleep stage of the subject based on one or both of the analyzed reactions and/or the one or more physiological parameters;
determine an accuracy of the estimation of the sleep stage;
determine whether the accuracy of the estimation of the sleep stage breaches a predetermined threshold; and
responsive to the accuracy of the estimation of the sleep stage failing to breach the predetermined threshold, perform one or more iterations of the following operations until the accuracy of the estimation of the sleep stage breaches the predetermined threshold:
control the stimulus source to provide a reassessment stimulus to the subject, wherein the reassessment stimulus comprises one or more stimuli of increasing intensity and/or varying modality;
analyze a reaction to the reassessment stimulus; and
reassess one or both of the estimation of the sleep stage and/or the accuracy of the estimation of the sleep stage based on the analyzed reaction to the reassessment stimulus.

2. The system of claim 1, wherein the one or more hardware processors are further configured to determine the one or more physiological parameters based on the generated output signals.

3. The system of claim 1, wherein the one or more physiological parameters pertain to brain function of the subject, the one or more physiological parameters that pertain to brain function comprising electroencephalography (EEG), electromyography (EMG), and/or electrooculography (EOG) parameters.

4. The system of claim 1, wherein the one or more physiological parameters pertain to movement of the subject.

5. The system of claim 1, wherein the one or more hardware processors are further configured to determine effectiveness of different stimuli to evoke reactions corresponding to a higher accuracy of the estimation of the sleep stage, wherein effectiveness is quantified by a difference between a level of intensity of a particular stimulus and a predetermined maximum level of intensity for the particular stimulus.

6. A method for facilitating sleep stage detection with a detection system, the detection system comprising a stimulus source, one or more sensors, and one or more hardware processors, the method comprising:
providing, with the stimulus source, stimuli to a subject;
generating, with the one or more sensors, electronic output signals conveying information related to one or more physiological parameters of the subject;
analyzing, with the one or more hardware processors, based on the one or more physiological parameters, reactions to the stimuli;
generating, with the one or more hardware processors, an estimation of a sleep stage of the subject based on the one or more physiological parameters;
determining, with the one or more hardware processors, an accuracy of the estimation of the sleep stage;
determining, with the one or more hardware processors, whether the accuracy of the estimation of the sleep stage breaches a predetermined threshold; and
responsive to the accuracy of the estimation of the sleep stage failing to breach the predetermined threshold, performing one or more iterations of the following operations until the accuracy of the estimation of the sleep stage breaches the predetermined threshold:
controlling, with the one or more hardware processors, the stimulus source to provide a reassessment stimulus to the subject, wherein the reassessment stimulus comprises one or more stimuli of increasing intensity and/or varying modality;
analyzing, with the one or more hardware processors, a reaction to the reassessment stimulus based on one or more physiological parameters; and
reassessing, with the one or more hardware processors, one or both of the estimation of the sleep stage and/or the accuracy of the estimation of the sleep stage based on the analyzed reaction to the reassessment stimulus.

7. The method of claim 6, further comprising:
determining the one or more physiological parameters based on the generated output signals.

8. The method of claim 6, wherein the one or more physiological parameters pertain to brain function of the subject, the one or more physiological parameters that pertain to brain function comprising electroencephalography (EEG), electromyography (EMG), and/or electrooculography (EOG) parameters.

9. The method of claim 6, wherein the one or more physiological parameters pertain to movement of the subject.

10. The method of claim 6, further comprising:
determining effectiveness of different stimuli to evoke reactions corresponding to a higher accuracy of the estimation of the sleep stage, wherein effectiveness is quantified by a difference between a level of intensity of a particular stimulus and a predetermined maximum level of intensity for the particular stimulus.

11. A system configured to facilitate sleep stage detection, the system comprising:
means for providing stimuli to a subject;
means for generating output signals conveying information related to one or more physiological parameters of the subject;
means for analyzing reactions to the stimuli, wherein operations of the means for analyzing is based on the one or more physiological parameters;
means for generating an estimation of a sleep stage of the subject based on the one or more physiological parameters;
means for determining an accuracy of the estimation of the sleep stage;
means for determining whether the accuracy of the estimation of the sleep stage breaches a predetermined threshold;
responsive to the accuracy of the estimation of the sleep stage failing to breach the predetermined threshold, means for performing one or more iterations of the following operations until the accuracy of the estimation of the sleep stage breaches the predetermined threshold:
means for controlling the means for providing stimuli to provide a reassessment stimulus to the subject, wherein the reassessment stimulus comprises one or more stimuli of increasing intensity and/or varying modality;
means for analyzing a reaction to the reassessment stimulus based on one or more physiological parameters; and
means for reassessing one or both of the estimation of the sleep stage and/or the accuracy of the estimation of the sleep stage based on the analyzed reaction to the reassessment stimulus.

12. The system of claim 11, further comprising:
means for determining the one or more physiological parameters based on the generated output signals.

13. The system of claim 11, wherein the one or more physiological parameters pertain to brain function of the subject, the one or more physiological parameters that pertain to brain function comprising electroencephalograph); (EEG), electromyography (EMG), and/or electrooculography (EOG) parameters.

14. The system of claim 11, wherein the one or more physiological parameters pertain to movement of the subject.

15. The system of claim 11, further comprising:
means for determining effectiveness of different stimuli to evoke reactions corresponding to a higher accuracy of the estimation of the sleep stage, wherein effectiveness is quantified by a difference between a level of intensity of a particular stimulus and a predetermined maximum level of intensity for the particular stimulus.

16. The system of claim 1, wherein the one or more hardware processors are further configured to adjust intensity of the stimuli and/or the reassessment stimulus provided to the subject based on a level of environmental ambient noise.

17. The method of claim 6, wherein the intensity of the stimuli and/or the reassessment stimulus provided to the subject is adjusted, by the one or more hardware processors, based on a level of environmental ambient noise.

18. The system of claim 11, wherein the intensity of the stimuli and/or the reassessment stimulus provided to the subject is adjusted based on a level of environmental ambient noise.

* * * * *